United States Patent [19]

Bacaner

[11] Patent Number: 5,036,106

[45] Date of Patent: Jul. 30, 1991

[54] METHODS FOR THE TREATMENT OF DISORDERS OF THE CARDIAC VASCULAR SYSTEM

[76] Inventor: Marvin B. Bacaner, 4401 Fremont Ave. South, Minneapolis, Minn. 55419

[21] Appl. No.: 403,128

[22] Filed: Sep. 5, 1989

[51] Int. Cl.$^5$ .................. A61K 31/13; A61K 31/14; A61K 31/135

[52] U.S. Cl. ................................ 514/643; 514/656; 514/659

[58] Field of Search .................. 514/643, 656, 659

[56] References Cited

U.S. PATENT DOCUMENTS 4,001,433  1/1977  Maxwell et al. .................. 514/643

*Primary Examiner*—Stanley J. Friedman

[57] ABSTRACT

Methods are described to utilize synergistic interactions by various combinations of (1) bethanidine and various tricyclic compounds, (2) bethanidine and bretylium tosylate, (3) bretylium tosylate and various tricyclic compounds, and (4) debrisoquin sulfate and various tricyclic compounds, preferably in a single injectable or oral dosage form, to prevent, treat, and reduce the vulnerability of the heart to ventricular fibrillation and other ventricular arrhythmias in animals, both human and otherwise. Also, the use of bethanidine and bretylium tosylate in combination, and the use of debrisoquin sulfate for the resuscitation of pulseless beings, the use of debrisoquin sulfate for the suppression of ventricular fibrillation and ventricular tachycardia, and the use of bethanidine as an antidote to tricyclic antidepressant toxicity are disclosed.

5 Claims, No Drawings

METHODS FOR THE TREATMENT OF DISORDERS OF THE CARDIAC VASCULAR SYSTEM

FIELD OF THE INVENTION

Background of the Invention

This invention is directed to methods for the treatment of disorders of the cardiac vascular system. More particularly, the invention is directed to methods for the suppression of cardiac arrhythmias, particularly ventricular fibrillation, utilizing synergistic interactions by combining bethanidine, bretylium tosylate or debrisoquin sulfate and certain tricyclic compounds in injectable or oral dosage form. The invention includes the use of combinations of bethanidine and bretylium tosylate for acute cardiac resuscitation of pulseless humans in a single injectable or oral dosage form to prevent, treat, and reduce the vulnerability of the heart to ventricular fibrillation and other ventricular arrhythmias, and to improve and stabilize the electrical and mechanical performance of the heart and circulation in animals, both human and otherwise. The invention is also directed to the use of debrisoquin sulfate for the suppression of ventricular fibrillation and ventricular tachycardia, and to the use of bethanidine as an antidote to tricyclic compound overdose toxicity.

Bethanidine sulphate and bretylium tosylate are prototype antifibrillatory drugs that specifically decrease the vulnerability of the mammalian heart ventricles to undergo and sustain ventricular fibrillation by increasing ventricular fibrillation threshold and inducing the phenomenon of non-sustained ventricular fibrillation, thereby reducing vulnerability of the heart to ventricular fibrillation. Both drugs also cause post-ganglionic sympathetic blockade and were originally introduced as antihypertensive agents designed to lower blood pressure by blocking adrenergic transmitter release. However, neither drug has been marketed in the United States as an antihypertensive agent because the major effect is on orthostatic (positional) hypotension with little or no effect on supine blood pressure. Moreover, newer methods of controlling blood pressure have rendered their use in treatment of hypertension obsolete. In addition, tolerance to the orthostatic effects of bretylium tosylate and bethanidine, which gradually occurs after therapy has been started, limits even this effect.

However, the antifibrillatory actions of bethanidine and bretylium tosylate on the mammalian ventricle have important clinical applications. Bretylium tosylate is presently marketed in the United States for the "prophylaxis and therapy of ventricular fibrillation" as well as other life-threatening arrhythmias.

During clinical trials of bretylium tosylate and bethanidine for use in suppressing arrhythmias and in preventing ventricular fibrillation, it was found that ambulation of the patient was almost impossible initially because of a severe drop in blood pressure on assuming the upright position (orthostatic hypotension) which caused dizziness and syncope (loss of consciousness). Until tolerance to the hypotensive effect appeared, it was very difficult to get patients with persistent life-threatening arrhythmias who required continued treatment with bretylium tosylate or bethanidine out of bed or to discharge them from the hospital for long periods of time while these drugs were being administered.

A number of approaches to antagonize the orthostatic hypotensive side effects of bretylium tosylate and bethanidine have been undertaken because of the desperate need for a drug to prevent ventricular fibrillation in cardiac patients with a known and predictable risk of suffering sudden death. These risks include patients during the early phase of acute myocardial infarction and patients with hemodynamically unstable ventricular arrhythmias, as well as patients who have been resuscitated from previous episodes of ventricular fibrillation, particularly in the absence of an acute myocardial infarction.

Debrisoquin sulfate is a post ganglionic blocking drug which was designed to treat hypertension, like bretylium and bethanidine. Its use for this purpose was rendered obsolete by newer and more effective methods of lowering blood pressure.

The Prior Art

Many drugs have been investigated for their ability to counteract the orthostatic hypotension of bretylium tosylate. These include effedrine, dexamphetamine, several amine oxydase inhibitors and tricyclic antidepressants.

SUMMARY OF THE INVENTION

Broadly stated, the invention comprises a method for suppressing cardiac ventricular arrhythmias, particularly ventricular fibrillation, in living beings by administering bethanidine, bretylium tosylate or debrisoquin sulfate to those beings in a small but effective amount at least sufficient to restore sinus rhythm, along with a small but effective synergistic interacting amount of a tricyclic compound. The invention also comprises a method for managing cardiac resuscitation of pulseless humans by intravenous injection of a combination of bethanidine and bretyliumtosylate, or of debrisoquin. In addition, the invention comprises a method for treating cardiovascular collapse caused by toxic overdose of tricyclic antidepressant compounds in living beings by administration of intravenous bethanidine in a small but effective amount sufficient to reverse the toxic response.

DETAILED DESCRIPTION OF THE PREFERRED EMBODIMENT

The present invention utilizes synergistic interactions by various combinations of (1) bethanidine and tricyclic compounds, (2) bethanidine and bretylium tosylate, (3) bretylium tosylate and tricyclic compounds, and (4) debrisoquin sulfate and tricyclic compounds, preferably in a single injectable or oral dosage form to prevent, treat, and reduce the vulnerability of the heart to ventricular fibrillation and other ventricular arrhythmias in animals both human and otherwise. Suitable tricyclic compounds include protriptyline, mazindol, amitriptyline, nortriptyline, desipramine, and similar substituted compounds having three fused rings, most of which are useful as antidepressant drugs. For example, desipramine, mazindol or protriptyline in small doses do not raise ventricular fibrillation threshold. While doses of these drugs greater than 4 mg/kg do raise ventricular fibrillation threshold, these high doses often cause toxic cardio-circulatory collapse and therefore such doses cannot be used safely in patients on a chronic basis. Low doses of bethanidine have only marginal effects on ventricular fibrillation threshold. The most effective suppression of ventricular fibrillation by bethanidine or bretylium tosylate requires doses of 20 to 30 mg/kg.

However, combining bethanidine or bretylium tosylate with sub-therapeutic doses of a variety of tricyclic compounds induces a synergistic interaction such that the ventricular fibrillation threshold increases to a significantly greater level than can be achieved additively with either drug alone. Antifibrillatory synergism has been found for protriptyline, amitriptyline, desipramine, nortriptyline and mazindol Similarly, bethanidine and bretylium tosylate given together induce a greater resistance to ventricular fibrillation by blocking potassium channels in the cardiac membrane than similar doses of either drug given alone may induce. Bethanidine, which is much more rapidly absorbed than bretylium alone, speeds the onset of antifibrillatory action, where survival is completely dependent upon how rapidly the heartbeat is restored. Addition of bethanidine augments the magnitude of the increase in ventricular fibrillation threshold and speeds the onset of antifibrillatory action faster than bretylium tosylate alone. This is due to synergistic electrophysiologic effects which reduce the heterogeniety of electrical excitability (action potential configuration) of cardiac cells. Moreover, this combination also augments by increasing heart rate, cardiac output, and blood pressure the mechanical performance of the heart by greatly increasing catecholamine release. The latter combination of electrical and mechanical actions are ideal in the emergency treatment of pulseless cardiac arrest. A prior diagnosis distinguishing between ventricular fibrillation and cardiac standstill or severe bradycardia would not have to be made. A combination of bethanidine and bretylium tosylate would be effective against either condition. By not requiring a diagnosis of the underlying cause of pulseless cardiovascular collapse, the immediate administration of intravenous or intracardiac bethanidine-bretylium tosylate combination saves the time and expertise needed to establish a diagnosis to distinguish between ventricular fibrillation and cardiac standstill which ordinarily require different treatments (i.e., electric shock for ventricular fibrillation and catecholamine administration for cardiac standstill or bradycardia and hypotension). Administration can thus be undertaken by less skilled persons than are now required to make decisions on treatment to be used. Thus, by utilizing the synergistic interaction between bethanidine or bretylium tosylate and tricyclic compounds, or between bethanidine and bretylium tosylate, the dose of both drugs needed to achieve a therapeutic increase in ventricular fibrillation threshold is reduced, thereby minimizing or eliminating toxic and/or deleterious side effects of the individual drugs on the mechanical performance of the heart. In addition, a bethanidine-bretylium tosylate combination can be used to augment mechanical performance of the heart during depressed, low cardiac output states or cardiogenic shock to increase contractile strength, heart-rate, and increase blood pressure. This makes the bethanidine-bretylirm tosylate combination useful for immediate initial treatment of cardiac arrest without a prior diagnosis of fibrillation standstill, or tachycardia by less skilled personnel, such as paramedics. If the arrest is due to either ventricular fibrillation or cardiac standstill, the antifibrillatory effect will help establish a rhythmic beat while the vasoconstrictor and cadiotomic effects of initial catecholamine release will stimulate impulse formation, increase heart rate, and increase peripheral resistance. The latter will make closed chest cardiac massage more effective because vaso-constriction of the peripheral vessels will force a greater fraction of the blood expelled during chest compressions to go to the coronary arteries and arteries to the brain selectively because these vessels are not vaso-constricted by catecholamines released by the bethanidine-bretylium tosylate combination in contrast to the other parts of the peripheral circulation which are vaso-constricted by catecholamine release.

The various drug combinations may be prepared for administration orally or by intravenous injection. The bethanidine or bretylium tosylate combination with a tricyclic compound is administered in doses of from about 5 to 30 mg per kilogram of body weight of bethanidine or bretylium tosylate with a subtherapeutic dose of the tricyclic compound. Such subtherapeutic doses of the tricyclic compound vary with the compound, as follows: for protriptyline, about 2 to 10 mg/dose; for amitriptyline, about 3 to 30 mg; for nortriptyline, about 2 to 20 mg; for desipramine, about 2 to 20 mg; and for mazindol, about 0.2 to 10 mg. By way of example, a convenient tablet form may contain from 250 to 500 mg bethanidine combined with from 2.5 to 5 mg protriptyline. The bethanidine-bretylium tosylate combination is administered in doses of from about 5 to 20 mg/kg/dose of each drug. Bretylium in amount 10 mg/kg/dose is combined with 2 mg to 10 mg protriptyline in the dose.

Combining debrisoquin with various tricyclic compounds has a synergistic interaction increasing ventricular fibrillation threshold like bretylium and bethanidine interactions. Debrisoquin may be administered in doses of about 3 to 15 mg/kg of body weight in combination with the tricyclic compounds, protriptyline, amitriptyline, nortriptyline, desipramine or mazindol.

Natural tolerance to orthostatic hypotension caused by bretylium tosylate commonly develops after bretylium tosylate has been administered for some time, which was one of the reasons for its therapeutic failure as an antihypertensive agent. Thus, the reported successful reversal of bretylium tosylate induced orthostatic hypotension with protriptyline could not completely exclude the development of tolerance to bretylium tosylate as a cofactor rather than a pure action of the protriptyline per se. Since tolerance to orthostatic hypotension induced by bethanidine is very slow to occur, the effect of protriptyline and other tricyclic compounds on bethanidine induced orthostatic hypotension had to be tested. It was found that protriptyline amitriptyline, mazindol, desipramine and nortriptyline (all tricyclic compounds tested) did in fact antagonize orthostatic hypotension induced by bethanidine in a similar fashion to its interaction with bretylium tosylate. Therefore, combined therapy of bethanidine with tricyclic compounds was a potentially useful clinical treatment to aid the ambulation of patients treated with bethanidine or bretylium tosylate.

Drug Interactions of bretylium tosylate and bethanidine with tricyclic compounds on ventricular fibrillation threshold (VFT).

While combinations of bretylium tosylate and tricyclic compounds were apparently useful in antagonizing the orthostatic hypotensive effect of bretylium tosylate (and bethanidine) on the peripheral vascular system it was necessary to determine their effects on ventricular fibrillation threshold (VFT) to be certain that the pharmacological antagonism on blood pressure did not also antagonize the therapeutic effect of bretylium tosylate and bethanidine on raising electrical ventricular fibrillation threshold.

Studies were therefore carried out to measure (1) the dose dependent effect on VFT of various tricyclic compounds alone, (2) the effect on VFT of bretylium tosylate combined with tricyclic compounds, (3) the effect of bethanidine combined with tricyclic compounds, and (4) the effect of bethanidine combined with bretylium tosylate.

The electrophysiologic and mechanical interactions of bethanidine and bretylium tosylate.

Bretylium tosylate prolongs action potential duration on cardiac cells and has been classified as a class 3 antiarrhythmic drug. Bethanidine, in contrast, is not reported to increase action potential duration in dogs, but does in rat hearts. To investigate their interactions on VFT, subtherapeutic doses of both bretylium tosylate (5 mg/kg) and bethanidine (5 mg/kg) were given in a single injection to five dogs.

In the normal dog heart, bretylium (5 mg/kg) alone raised VFT an average of 69%. Bethanidine (5 mg/kg) alone raised VFT an average of 72%. When the two drugs were given together (2.5 mg/kg each), VFT increased 220% and many of the hearts became non-fibrillatable at the peak current output of the generator.

Typical effects of tricyclic compounds on VFT.

As an example of the typical effect of a tricyclic compound, the effect of various doses of protripty-line (0.5–10 mg/kg) on ventricular fibrillation threshold (VFT) were studied in 11 dogs. The results are shown in Table 1.

TABLE 1

| | Dose of Protriptyline (mg/kg) | Avg Control VFT (ma) | Avg VFT (ma) after protriptyline | Avg % Change |
|---|---|---|---|---|
| Dose | 0.5 | 26 | 28 | +3.89% |
| Dependent | 1.0 | 23.5 | 23 | −1.9% |
| Progressive | 2.0 | 20 | 29 | +45% |
| Cardiac | 3.0 | 26 | 38.5 | +44% |
| Toxicity | 4.0 | 17 | 32 | +80% |
| Occurs | 5.0 | 17 | 38 | 123.5% |
| | 10.0 | 22 | 70 | +218% |

In doses of 1 mg/kg, or less, protriptyline had no significant effect on VFT. In doses of 2 to 3 mg/kg protriptyline induced a modest (44.5%) increase in VFT. Doses above this level produced a significant dose dependent increase in VFT (Table 1). A 10 mg/kg dose of protriptyline induced a 218 per cent increase in VFT. However, doses of 2 mg/kg or greater cannot be used safely because of toxicity on the cardiovascular system, often causing toxic cardio-circulatory collapse. Similar dose response effects were found with other tricyclic compounds, such as desipramine, amitriptyline, nortriptyline and mazindol.

Effects of the interactions of bethanidine and protriptyline on VFT.

The interaction of protriptyline followed by bretylium and vice versa are shown in Tables 2 and 3, respectively.

TABLE 2

| | Protriptyline followed by bretylium | | |
|---|---|---|---|
| | Avg. Control VFT (ma) | Avg. VFT (ma) after protriptyline (0.5 mg/kg) | Avg. VFT (ma) after adding bretylium (5 mg/kg) |
| Normal heart | 25 | 29 (+16%) | 70 (+180%) |
| Infarcted heart | 12.7 | 17 (+33%) | 32.9 (+159%) |

TABLE 3

| | Bretylium followed by protriptyline | | |
|---|---|---|---|
| | Avg. Control VFT (ma) | Avg. VFT (ma) after bretylium (5 mg/kg) | Avg. VFT (ma) after adding protriptyline (0.5 mg/kg) |
| Normal heart | 24.3 | 57.3 (+94.6%) | 79.7 (238%) |
| Infarcted heart | 20 | 35.5 (+77.5%) | 50.4 (150%) |

It is apparent from the data in Tables 1 and 2 that small doses of protriptyline (0.5 to 1 mg/kg) had no significant effect on VFT in either the normal or infarcted heart. Low doses of bretylium (5 mg/kg or less) have only marginal effects on ventricular fibrillation threshold. In Table 3 it can be seen that bretylium (5 mg/kg) induced only a moderate increase in VFT of 94.6% in the normal heart and 77.5% in the infarcted heart (Table 3). However, as shown in Table 3, the subsequent addition of subtherapeutic doses of protriptyline (0.5 to 1 mg/kg) which alone had little effect on VFT (Tables 1 and 2), had a profound synergistic interaction with bretylium which caused a further significant increase in VFT to 238% in the normal heart and 150% in the infarcted heart.

Table 2 shows that when a subtherapeutic dose of protriptyline (0.5 mg/kg) was given first, there was little effect on VFT. However, the subsequent administration of 5 mg/kg bretylium caused a profoundly greater increase in VFT in both the normal (180%) and infarcted heart (159%) than a 5 mg/kg dose of bretylium, could induce when given alone (94.6% and 77.5%, respectively; Table 3).

When bretylium (10 to 20 mg/kg) and protriptyline (0.5 mg/kg) were given together as a single injection, the normal heart was often made invulnerable to electrically induced sustained ventricular fibrillation at the highest output of our current generator (100 ma train of impulses at 100 Hertz). This protective effect is not commonly achieved by bretylium without protriptyline.

It has been clearly shown that by combining suitable doses of bretylium or bethanidine (5 to 20 mg/kg), and low doses of protriptyline in a single dosage form, a synergistic interaction occurs that increases VFT to a much greater level than either drug alone can achieve. A major advantage of this interaction is the ability to (a) amplify the antifibrillatory effect of both drugs and (b)

utilize the antifibrillatory action of protriptyline which without bretylium or bethanidine would require doses of protriptyline that cannot be used without severe toxicity that could cause cardiovascular collapse. Similar results were observed with combinations of bethanidine and bretylium tosylate with the other tricyclic compounds tested, desipramine, nortriptyline, amitriptyline and mazindol Effects of the interaction of bretylium tosylate and desipramine on VFT.

The typical interaction between bretylium tosylate and a tricyclic compound was shown by the combination of minimal therapeutic doses of bretylium tosylate (5 mg/kg) and desipramine (1 mg/kg) which causes a dramatic increase in ventricular fibrillation threshold that exceeds the effect when either drug is given alone. This combination raises ventricular fibrillation threshold an average of 480%. In contrast, 5 mg/kg bretylium tosylate increased ventricular fibrillation threshold (VFT) 110%, whereas 1 mg/kg desipramine has no effect on VFT. Three mg/kg desipramine increases VFT by an average of 78%, but this dosage is close to toxic levels, particularly if given chronically.

Bethanidine as an antidote to tricyclic antidepressant toxicity.

A further action of bethanidine is a capacity to counteract the cardiovascular collapse (arrhythmias together with hypotensive shock) caused by toxic overdose of the tricyclic antidepressants protriptyline and amitriptyline by suicidal patients treated with these agents for depression. In doses of 10 to 20 mg/kg bethanidine improves the rhythm stability and reverses circulatory collapse that results from tricyclic antidepressant overdose. In eight dogs doses of tricyclic antidepressants (amitripyline or protriptyline, 4 to 20 mg/kg) were infused until they caused shock, heart failure and severe arrhythmia. The subsequent administration of bethanidine in doses of 10 to 20 mg/kg reversed all of these toxic responses, and promoted survival in 4 of 8 animals that would have died if untreated. The beneficial effect on cardiocirculatory hemodynamics and survival of bethanidine on tricyclic overdose toxicity could not be demonstrated with bretylium tosylate. Although the administration of bretylium tosylate did tend to suppress arrhythmias, there was no significant recovery of blood pressure and the animals could not be revived.

Debrisoquin sulfate raises ventricular fibrillation threshold and causes non-sustained fibrillation (or spontaneous defibrillation). Because of these actions it can be used as an anti-arrhythmic antifibrillatory drug to treat and prevent ventricular dysrhythmias similar to bretylium and bethanidine. Doses from about 3 to 15 mg/kg cause a progressive increase in ventricular fibrillation threshold. Moreover, debrisoquin also causes a marked increase in blood pressure by catecholamine release that makes its use valuable for resuscitation of pulseless patients.

Debrisoquin given to 7 dogs made 5 of them invulnerable to electrically induced ventricular fibrillation at the peak current output (100 milliamperes) of the available generator. The other 2 dogs had increases in ventricular fibrillation threshold of 140% and 312%, respectively. Spontaneous restoration of sinus rhythm was observed after short runs of ventricular tachycardia and fibrillation in 3 animals.

It is apparent that many modifications and variations of this invention as hereinbefore set forth may be made without departing from the spirit and scope thereof. The specific embodiments described are given by way of example only, and the invention is limited only by the terms of the appended claims.

What is claimed is:

1. A method for suppressing cardiac ventricular arrhythmias in living beings which comprises administering bretylium tosylate to said beings in a small but effective amount at least sufficient to restore sinus rhythm along with small but effective synergistic interacting amount of a tricyclic compound selected from the group consisting of protriptyline, amitriptyline, nortriptyline, desipramine and mazindol.

2. A method according to claim 8 wherein said drugs are administered simultaneously in combination.

3. A method according to claim 8 wherein said drugs are administered orally.

4. A method according to claim 8 wherein said drugs are administered intravenously.

5. A method according to claim 1 wherein said bretylium is administered in an amount between about 5 mg. to 30 mg. per kilogram of body weight and said tricyclic compound is desipramine administered in an amount between about 2 mg. and 10 mg. per dose.

* * * * *

UNITED STATES PATENT AND TRADEMARK OFFICE
CERTIFICATE OF CORRECTION

PATENT NO. : 5,036,106

DATED : July 30, 1991

INVENTOR(S) : MARVIN B. BACANER

It is certified that error appears in the above-identified patent and that said Letters Patent is hereby corrected as shown below:

Col. 8, line 17, the hyphen "-" between "The" and "other" should be deleted.

Col. 8, line 37, "8" should be -- 1 ---.

Col. 8, line 39, "8" should be --- 1 ---.

Col. 8, line 41, "8" should be --- 1 ---.

Signed and Sealed this

Nineteenth Day of January, 1993

*Attest:*

DOUGLAS B. COMER

*Attesting Officer*     Acting Commissioner of Patents and Trademarks